United States Patent [19]

Fields et al.

[11] Patent Number: 4,585,897
[45] Date of Patent: Apr. 29, 1986

[54] PROCESS FOR PREPARATION OF FUEL ADDITIVES FROM ACETYLENE

[75] Inventors: Ellis K. Fields, River Forest; Mark L. Winzenburg, Naperville; David A. De Marco, Aurora, all of Ill.

[73] Assignee: Standard Oil Company (Indiana), Chicago, Ill.

[21] Appl. No.: 643,785

[22] Filed: Aug. 24, 1984

[51] Int. Cl.$^4$ .............................................. C07C 45/26
[52] U.S. Cl. ..................................... 568/409; 568/491; 568/451; 568/342; 568/387; 568/365; 568/311; 568/897; 568/429; 568/716; 585/416
[58] Field of Search ............... 568/491, 409, 451, 342, 568/387, 365, 311, 897, 429, 716; 585/897, 416

[56] References Cited

U.S. PATENT DOCUMENTS

| | | | |
|---|---|---|---|
| 1,779,676 | 10/1930 | Martin et al. | 568/409 |
| 3,082,269 | 3/1963 | Armitage | 585/416 |
| 3,204,008 | 8/1965 | Scheller et al. | 585/416 |
| 3,365,510 | 1/1968 | Noakes | 585/416 |
| 4,009,219 | 2/1977 | Tames | 585/416 |

FOREIGN PATENT DOCUMENTS

| | | | |
|---|---|---|---|
| 802510 | 10/1958 | United Kingdom | 585/416 |
| 824543 | 12/1959 | United Kingdom | 585/416 |

OTHER PUBLICATIONS

Spaenig et al, Chem. Abst., vol. 57, #8743h (1963).
Grenko et al, Chem. Abst., vol. 40, #6249 (1946).

*Primary Examiner*—James H. Reamer
*Attorney, Agent, or Firm*—William C. Clarke; William T. McClain; William H. Magidson

[57] ABSTRACT

A process for hydration and condensation of acetylene in a crude acetylene stream containing water in the presence of a zirconia-alumina catalyst containing water to prepare aliphatic, aromatic and oxygenated compounds suitable for use as high octane liquid water fuels and as octane improvers for motor fuels is disclosed.

7 Claims, No Drawings

PROCESS FOR PREPARATION OF FUEL ADDITIVES FROM ACETYLENE

FIELD OF THIS INVENTION

The field of this invention relates to a process for the liquefaction of acetylene streams containing water by selective hydration and condensation of acetylene and acetylenic compounds to aliphatic, aromatic and oxygenated compounds, in the presence of a zirconia-alumina catalyst, which are thereupon suitable for hydrogenation to compounds suitable for use as motor fuel additives to improve octane and as high octane motor fuels.

It is an object of this invention to provide a process for hydration and subsequent condensation of acetylene in a crude acetylene stream in the presence of substantial amounts of water to produce predominantly oxygenated compounds.

It is an object of this invention to provide a process for condensation of acetylene in a crude acetylene stream to produce predominantly aromatic hydrocarbons or aliphatic and aromatic hydrocarbons wherein the presence of water is about 3 (mole)% or less.

It is an object of this invention to provide a process for condensation of acetylene in a crude acetylene stream to produce aromatic hydrocarbons, or aliphatic and aromatic hydrocarbons, and hydration in the presence of water in a crude acetylene stream to produce oxygenated compounds. These aromatic, aliphatic and oxygenated compounds are suitable for use as octane improvers in motor fuels.

It is a further object of this invention to provide a process for utilization of a crude acetylene stream without first purifying the stream to obtain a purified acetylene.

It is a further object of this invention to provide a catalyst uniquely suited for condensation of acetylene and hydration of acetylene in the presence of water.

It is a further object of this invention to provide a catalyst and a process for the hydration and condensation of acetylene contained in a crude acetylene stream.

It is a further object of this invention to provide a process for the hydration and condensation of acetylene contained in a crude acetylene stream and to hydrogenate the products obtained therefrom.

It is a further object of this invention to provide a process for the condensation and hydration of acetylene wherein the presence of water prolongs catalyst activity in conversion of acetylene whereby increased presence of water results in low coke build-up on the catalyst.

These and other objects will become apparent from the description given hereafter.

BACKGROUND OF THIS INVENTION

This invention relates to the liquefaction of acetylene streams containing water by selective hydration and/or condensation in the presence of an alumina-zirconia catalyst. In particular, it concerns the hydration and/or condensation of acetylene and acetylenic compounds to aliphatic, aromatic and oxygenated compounds. These compounds are useful directly, or upon hydrogenation, as fuel additives to increase octane of motor fuel. It also concerns a process wherein presence of water in the crude stream results in lessened coke build-up on the catalyst, thus increasing catalyst life.

Acetylene and acetylenic compounds are produced by known technology from methane. Methane is cheap and abundant. Much of it occurs where no pipeline facilities exist, and it cannot be transported readily. However, methane can be converted to impure acetylene by partial combustion in the presence of air and by direct pyrolysis. A typical output stream from a methane oxidation plant producing a crude acetylene stream can be characterized as containing methane, carbon dioxide, oxygen, nitrogen, water, hydrogen, carbon monoxide, acetylene and acetylenic compounds. In cases where a higher hydrocarbon than methane is used as feedstock, the output stream also contains olefins such as ethylene, propylene, butadiene; aromatics such as benzene and naphthalene and miscellaneous higher hydrocarbons. Significant amounts of carbon black and tars are also produced.

Accordingly, a typical output stream from a methane pyrolysis plant contains acetylene, hydrogen, methane, ethylene, carbon monoxide, carbon dioxide, nitrogen and higher acetylenes (*Ency. Chem. Tech.*, 3rd, 1, 226).

The isolation of acetylene for further processing presents a complicated problem. The unstable, explosive nature of acetylene has required certain restrictions on use of separation systems utilized for other hydrocarbon systems. These restrictions indicate that partial pressure of acetylene should not exceed 15–30 psig to avoid possible decomposition and detonation. Similar limitations have been developed as to operating temperatures which should not be below 95°–105° C. Low temperatures can lead to the formation of liquid or solid acetylene or its homologs with attendant danger of decomposition. Because of these problems, processing and recovery of acetylene from a hydrocarbon oxidation process has typically been by absorption-desorption techniques using one or more selective solvents.

It has been unexpectedly found that a crude acetylene stream containing water can be processed over a zirconia-alumina catalyst without prior purification at temperatures of from about 200° C. to about 500° C. at atmospheric pressure to produce aromatic hydrocarbons, or aromatic hydrocarbons and aliphatic hydrocarbons or oxygenated compounds, depending upon the ratios of acetylene and water present. Other compounds normally present in the output of a crude acetylene process such as carbon dioxide, nitrogen, carbon monoxide, hydrogen and oxygen can also be present in the crude acetylene stream. The product mix of the hydration reaction can be utilized directly as motor fuel additives to improve octane or can be hydrogenated to obtain saturated compounds also suitable for use as motor fuel additives to improve octane. The presence of water also increases catalyst life by controlling the rate of coke build-up upon the catalyst.

It has long been known that pure acetylene can be copolymerized to benzene, styrene and higher aromatics. For example, U.S. Pat. No. 2,723,299 teaches the preparation of benzene and styrene from acetylene and vinylacetylene in a solvent with a catalyst, (triphenylphosphine) nickel dicarbonyl and a cocatalyst, copper ammonium halides. Dibenzylideneacetone-palladium(O) and platinum(O) complexes (*Chem. Communications* (1971), 1604), and cyclobutadiene-palladium halide complexes (*J. Organometal. Chem.*, 26, 407 (1971)) have been used for cyclotrimerizing acetylene and substituted acetylenes. U.S. Pat. No. 3,365,510 teaches the preparation of high purity benzene from acetylene by trimerization over a catalyst of activated alumina of surface area of 30 to 400 m²/g containing an oxide of V₂O₅, Nb₂O₅, Ta₂O₅, CrO₃, MoO₃, WO₃ or Mo₂O₅ in Group VB or VIB of the Periodic Table. U.S. Pat. No. 4,009,219 teaches the liquefaction of acetylene to aromatic hydrocarbons comprising principally benzene and alkylbenzenes by cyclotrimerization in the presence of a catalyst consisting of silica-alumina containing an oxide of chromium or vanadium in the strict absence of moisture in both the catalyst and the reacting acetylene.

Other previous teachings relate to processes for converting acetylenic hydrocarbons to aromatic hydrocarbons. For example, U.S. Pat. No. 2,217,009 teaches the conversion of 1-alkynes having 6 or more carbon atoms in straight chain arrangement at temperatures within the range of 450°–700° C., and contact times of 0.1 to 30 seconds with catalysts comprising a metal selected from the group consisting of titanium, zirconium, cerium, hafnium and thorium. Example III of U.S. Pat. No. 2,217,009 teaches zirconium dioxide on alumina catalyzes the production of benzene from hexyne-1. British Pat. No. 473,219 teaches preparation of monovinylacetylene, benzene, toluene, styrene and other aromatic compounds from acetylene in the presence of a catalyst containing a metal selected from the group consisting of metallic gold, molybdenum, silver and their alloys, also alloys containing iron, alumina, silicon and chromium, as well as oxides of titanium, zirconium and uranium. U.S. Pat. No. 2,819,325 teaches that liquid aromatic hydrocarbons comprising principally benzene and alkylbenzenes are obtained by the polymerization of 1-alkynes using a chromium oxide-containing catalyst comprising a catalyst support which is at least one member selected from the group consisting of silica, alumina, zirconia, titania, and siliceous natural clays over a wide range of temperature and pressure.

It has long been known that metals of Group IIB of the Periodic Table, as separate compounds or in the presence of alumina, are useful in preparing unsaturated compounds from acetylene. For example, U.S. Pat. No. 2,716,142 teaches the preparation of vinyl fluoride by reacting acetylene with hydrogen fluoride in the presence of a catalyst comprising particles of a zinc compound of the class consisting of zinc oxide, zinc nitrate and zinc sulfide. U.S. Pat. No. 2,634,300 teaches preparation of unsaturated monofluorides by reacting hydrogen fluoride with acetylenic hydrocarbons in the presence of a catalyst comprising alumina or aluminum fluoride, or alumina combined with other metals such as aluminum, antimony, cobalt, cadmium and zinc. U.S. Pat. No. 2,574,480 teaches the hydrofluorination of acetylene hydrocarbons in the presence of hydrogen fluoride and a catalyst comprising from 70 to 95 weight percent alumina and from 5 to 30 weight percent zinc fluoride. U.S. Pat. No. 3,413,361 teaches a process for production of vinyl fluoride from acetylene and hydrogen fluoride over a cadmium salt catalyst such as cadmium sulfate, cadmium nitrate, cadmium acetate or a mixture thereof.

Gas streams containing acetylenes and diolefins have been purified by selective hydrogenation of acetylenes using Group VIII metal catalysts. Typical hydrogenation processes are taught in U.S. Pat. Nos. 3,420,618 and 3,489,809, which are incorporated by reference.

It is also known that the condensation of acetylene and acetylenic compounds in the presence of water is often deleterious to the catalyst and to the catalytic reaction. For example, it is known that (triphenylphosphine) nickel dicarbonyl, as well as dibenzylideneacetone palladium complexes and alkyl palladium halide complexes, decompose in the presence of water. Strong Lewis acid catalysts such as those taught by U.S. Pat. No. 3,365,510 and U.S. Pat. No. 4,009,219 are also deactivated by the presence of water which is a Lewis base. U.S. Pat. No. 3,365,510 teaches that the synthesis of benzene from acetylene in the presence of Lewis acid catalysts is increased by thorough drying of the catalyst. U.S. Pat. No. 4,009,219 teaches that thorough drying of both the acetylene stream and the catalysts are very important to insure good yields and a low rate of catalyst deactivation. Accordingly, condensation of acetylene and acetylenic compounds is typically in an anhydrous environment, often in an organic solvent.

Acetaldehyde has long been produced by the addition of water to acetylene (S. A. Miller, "*Acetylene*" Vol. 2, Ernest Benn Limited, London, 1966; p 141–144). Commercially, aqueous mercuric sulfate solutions have been used to catalyze this reaction. The number of commercial vapor phase hydration processes is rather small. However, the catalyzed addition of water to acetylene by zinc compounds in the vapor phase was practiced in Germany during World War II (Miller, p. 146). The acetylene was saturated with water at 80° C., heated to 350° C. and passed through beds of zinc oxide. The principal product was acetone, about 60 carbon % yield, along with acetaldehyde and high ketones. Under comparable conditions, the instant process provides higher acetylene conversions and better organic liquid selectivities than available with zinc oxide based catalysts. The instant process in the presence of an alumina-zirconia catalyst not only tolerates the presence of water but results in the hydration and condensation of acetylene and acetylenic compounds to oxygenated compounds as well as condensation of acetylene and acetylenic compounds to aliphatic and aromatic compounds. The presence of water in the feed stream in the instant process is beneficial in that coke build-up on the catalyst is controlled.

Accordingly, a process has not been previously known for liquefaction of acetylene and acetylenic compounds in a crude acetylene stream containing water in the presence of a zirconia-alumina catalyst, to produce aliphatic, aromatic and oxygenated compounds at atmospheric pressure and temperatures within the range of from 200° C. to about 500° C.

SUMMARY OF THE INVENTION

Disclosed is a process for the liquefaction of acetylene in a crude acetylene stream containing water by hydration and condensation in the presence of a zirconia-alumina catalyst to prepare aliphatic, aromatic and oxygenated compounds suitable for use as high octane liquid motor fuels and as octane improvers for motor fuels.

DETAILS OF THE INVENTION

It has now been discovered that acetylene contained in an impure feed stream obtained in pyrolysis or partial oxidation of natural gas or methane containing water can be selectively hydrated, condensed and aromatized to form organic liquids, comprising aliphatic, aromatic and oxygenated liquid compounds suitable for use as high octane motor fuels or as octane improvers when blended with motor fuels in the presence of a zirconia-alumina catalyst wherein the catalyst has a surface area of 10 to about 100 m²/g and the surface zirconium to aluminum atomic ratio is from about 0.01:1 to about 1:1, preferably from 0.1:1 to 1:1 at a temperature within the range of from about 200° to about 500° C., and a pressure from about 0.5 to about 2 atmospheres, preferably from about 300° C. to about 500° C., and from 1.0 to 1.5 atmospheres.

The alumina content of the zirconia-alumina catalyst can be within the range of from about 1 (wt)% to about 20 (wt)%, preferably within the range of from about 1 (wt)% to about 5 (wt)%, more preferably within the range of from about 1 (wt)% to about 2.5 (wt)% since much greater conversion of acetylene and improved liquid yields are obtained with a catalyst containing a small amount of alumina. The bulk concentration of alumina is not critical, however.

A commercial zirconia-alumina composition labeled A in Table 1 is an excellent catalyst for the conversion of wet acetylene to a liquid consisting principally of aromatics in the presence of low amounts of moisture as in Example II or in the presence of about equal amounts of water to a mixture of aliphatic and aromatic oxygenates as shown in Example IV. This catalyst is characterized as having a bulk aluminum content of about 2 weight %, a surface area of about 40 to 50 square meters per gram, a pore volume of about 0.12 to 0.14 cubic centimeters per gram, and an average pore radius of about 40 Angstroms. In addition, the catalytic surface of this composition is enriched in aluminum relative to the bulk composition, having a surface aluminum:zirconium ratio by x-ray photoelectron spectroscopy of about 0.45:1.0 to 0.60:1.0.

A zirconia-alumina catalyst labelled B in Table I with 2% aluminum impregnated on zirconia thereupon was prepared, approximately the same bulk composition, surface area, and pore volume as the commercial zirconia-alumina catalyst A. The surface aluminum:zirconium ratio by x-ray photoelectron spectroscopy was 0.1:1. Comparison of Examples IV and V and/or Examples X and XI demonstrate that zirconia-alumina catalyst A is preferred to zirconia-alumina catalyst B. Both are active catalysts and selective for the liquefaction of acetylene.

Examples III, VI, VII, XII, XIII and XIV demonstrate that powdered zirconia alone or powdered zirconia admixed with or supported on a support such as active alumina or silica does not efficiently convert moist acetylene to organic liquids. Commercial $ZrO_2$ powder was found to be only 20% as active as precipitated $ZrO_2$ prepared experimentally. The reason for this difference results from the fact that the precipitated $ZrO_2$ has a higher surface area than commercial $ZrO_2$. Almost any solid material is capable of converting a small amount (5–10%) of acetylene to oligomeric material, probably by providing a surface for thermal reactions. As shown by Examples XIII and XIV, high surface area, active alumina is a better catalyst than low surface area zirconia.

Comparison of Examples V and VI demonstrates that zirconia-alumina catalyst B is twice as active for the conversion of moist acetylene as the precipitated zirconia from which it is prepared. Comparison of Examples XI and XII demonstrates that in the presence of higher levels of steam, the zirconia-alumina catalyst is 20% more active and yields almost two times as much organic liquid product as a catalyst consisting of precipitated zirconia supported in an alumina matrix.

In the prior art, the oligomerization-aromatization of acetylene has been associated with acid sites (P. Tsai and J. R. Anderson, *Journal of Catalysis*, 80, 207–214 (1983) and references therein).

As noted above, the greater activity of the alumina-containing zirconia catalysts is considered to be due to formation of acid sites by close interaction of aluminum and zirconium atoms. This is analogous to silica-alumina (since zirconium is a cogener of silicon) which is a stronger acid than either silica or alumina alone. A study of the commercial zirconia-alumina catalyst surface by x-ray photoelectron spectroscopy (XPS) shows zirconium and aluminum in an atomic ratio of 0.57 to 1. The zirconium-alumina catalyst B catalyst has a surface Al:Zr ratio of 0.1:1. Surface areas of the commercial zirconia-alumina catalyst and of the zirconia-alumina catalyst of the instant invention are approximately equal. Catalysts prepared by supporting zirconium oxide on alumina show aluminum:zirconium ratios of about 4:1 to about 10:1 and are much less active than the preferred catalysts of Al:Zr ratios of 0.1:1 to 1:1 despite having about the same surface area.

Water content of the crude acetylene stream can be in the range of from about 0.1 (mole)% to about 70 (mole)% at 25° C. at a pressure of from about 0.5 to 2.0 atmospheres.

Wet acetylene streams containing low amounts of water up to about 3 mole % water and up to about 97 mole % acetylene, such as a mole ratio of about 100:1, acetylene:water, an acetylene stream saturated with water vapor at room temperature (25° C.) having a mole ratio of about 35:1, acetylene:water, are by the process of this invention mainly converted to a mixture of aromatic hydrocarbons comprising benzene, alkylbenzene and higher aromatics useful as chemical feedstocks or fuel additives. Under these conditions the primary role of the zirconia-alumina catalyst is thought to be as a site for the cyclocondensation of three acetylene molecules to benzene. Cyclocodensations of larger numbers of acetylene molecules and subsequent reaction of aromatic nuclei with additional acetylene molecules yields the observed product slate.

Temperature of the instant invented process can be within the range of from about 200° C. to about 500° C., but lower and higher temperatures can be used as temperature is not especially critical. Pressure can be from 0.5 atmospheres to about 2 atmospheres. Extremely high pressures need to be avoided because of the formation of unstable acetylenic compounds.

The yield of liquid products obtained by conversion of acetylene streams by the process of this invention in the presence of zirconia-alumina catalysts is maximized when the mole ratio of acetylene:water is between 1:2 and 2:1. Under these conditions, the primary reaction is thought to be hydration of the acetylene to acetaldehyde. Subsequent reactions of acetaldehyde and its self-condensation products with acetylene and aromatic nuclei formed therefrom generate a broad spectrum of aromatic and aliphatic oxygenated products described in Example VIII and Table 4. Subsequent hydrogenation of this liquid product yields a mixture of alcohols suitable as a fuel additive.

Conversion of acetylene by the process of this invention in the presence of a large excess of water, such as water:acetylene mole ratios of about 4:1 to about 30:1 gives a high yield of acetaldehyde, ethanol, and acetone which can be easily hydrogenated to yield a high octane mixture of ethanol and isopropanol with a research blending octane number of about 120 suitable for use a octane improving fuel additive or as a co-solvent for methanol based fuel additive.

The zirconia-alumina catalyst of this invention can be used with acetylene mixed with CO, $CO_2$, $H_2O$, $H_2$, $CH_4$, or any combination of these, to convert the acetylene at 200°–500° C. and 0.5 to 2.0 atmospheres, preferably 300°–500° C. and 1.0–1.5 atmospheres pressure to products that are liquid at 25° C. or lower and that may be transported and used for fuels or chemicals. The catalyst can be used also to convert substituted acetylenes to aromatic compounds as chemical intermediates.

Catalyst activity in the conversion of acetylene has been found to be prolonged by the presence of water. Under conditions wherein a stream of 100% acetylene was fed to a reactor in the process of this invention the catalyst was heavily coked within a short period of time, requiring shutdown. In the presence of suitable amounts of water, as much as 70 (mole)% water, coke build-up was minimal.

overnight to decompose the nitrate to the oxide. Catalyst C is 80 wt% zirconia supported on gamma alumina. It was prepared by mixing 80 g of precipitated zirconia powder (catalyst E) and 20 g of alpha-alumina monohydrate with 5 wt% acetic acid to make a paste, drying at 120° C., and calcining at 1000° F. overnight to convert the matrix to gamma alumina. Catalyst D is also 80 wt% zirconia supported on gamma alumina. It was prepared in the same manner as catalyst C but employed a low surface area zirconia powder (catalyst F). Catalyst E is precipitated zirconia. It was prepared by slow addition of $Zr(n-OC_3H_7)_4$ (159.4 g) to about 900 ml of water. The resulting white solid was air dried and calcined at 1000° F. overnight. Catalyst F is zirconia powder purchased from Aldrich Chemical Co., Milwaukee, Wis. Catalyst G is gamma-alumina activated by calcining it overnight at 1000° F. All catalysts were ground and sieved to 18/40 mesh unless otherwise stated. Characterization of the catalysts is shown in Table 1.

TABLE 1

| Catalyst | Composition | Bulk Analysis, weight % | | | Surface Analysis, atom % | | | | Digisorb-Desorption | | Average Pore Radius, Angstroms |
|---|---|---|---|---|---|---|---|---|---|---|---|
| | | Al | Zr | Hf | C | O | Al | Zr | Surface Area $m^2/g$ | Pore Volume cc/g | |
| A | $ZrO_2$—$Al_2O_3$, (Alfa) | 1.4 | 73 | 1.4 | 6.9 | 60.0 | 12.0 | 21.1 | 44 | 0.128 | 40 |
| B | $ZrO_2$—$Al_2O_3$ (impregnated) | 1.5 | 71 | 1.8 | 14.1 | 55.8 | 2.4 | 27.7 | 40 | 0.1961 | 228 |
| C | 80% $ZrO_2$(E)/$Al_2O_3$ | 12 | 57 | 1.2 | | 57.8 | 37.7 | 4.3 | 51 | 0.1717 | 50 |
| D | 80% $ZrO_2$(F)/$Al_2O_3$ | 9.8 | 60 | 0.9 | | 59.8 | 32.7 | 7.5 | 45 | 0.1315 | 34 |
| E | $ZrO_2$, precipitated | | 72 | 1.8 | | | | | 56 | 0.242 | 228 |
| F | $ZrO_2$, (Aldrich) | | 73 | 1.5 | | | | | 1 | a | a |
| G | gamma-alumina | 59.2 | | | | | | | 195 | 0.5679 | 38 | a = surface area too small for accurate determination

In summary, the invented process comprises a process for hydration and condensation of acetylene and acetylenic compounds in a crude acetylene stream containing water in the presence of a zirconia-alumina catalyst wherein alumina content is in the range from 1 (wt)% to about 10 (wt)%, the zirconia surface area of said catalyst is from about 10 to about 100 $m^2/gm$, the surface aluminum:zirconium (Al:Zr) atomic ratio is 0.01:1 to 20:1, water content at 25° C. of said stream is in the range of from about 0.1 (mole)% to about 70 (mole)%, and acetylene to water mole ratio is from about 100:1 to about 1:35 at a temperature within the range of from about 200° to 500° C. and a pressure of from about 0.5 to 2.0 atmosphere. Preferably said alumina content is in the range of from 1 (wt)% to about 2.5 (wt)% and said surface aluminum:zirconium atomic ratio is in the range of 0.1:1 to 1:1. The said crude acetylene stream can contain methane, carbon dioxide, oxygen, nitrogen, water, hydrogen, carbon monoxide, acetylene and acetylenic compounds.

The invention will be illustrated by reference to the following specific examples. All percentages are in weight percentages unless otherwise designated.

EXAMPLE I

Seven catalysts were used in the following examples. Catalyst A is zirconia-alumina (98 wt% $ZrO_2$) purchased from Alfa Products, Thiokol/Ventron Div., Danvers, Mass. As received, it was in the form of medium gray ⅛" pellets. It was calcined overnight at 1000° F. after which it became white. Catalyst B is a zirconia-alumina of approximately the same composition as catalyst A. It was prepared by impregnating precipitated zirconia (38.06 g) with a solution of aluminum nitrate hexahydrate (5.9 g) in 50 ml of water. The catalyst was dried at 110° C. overnight and calcined at 1000° F.

EXAMPLE II 50 ml of ⅛" pellets of zirconia-alumina catalyst A were calcined in air flowing at 300 cc/min at 450° C. for 1.25 hours, and cooled to 200° C. under nitrogen at 100 cc/min. The gas stream was switched to acetylene bubbled from a cylinder through a column of 6" of water at 25° C. and passed directly into the tube containing the catalyst. Over 2.5 hours, 1.2 ml of light green liquid condensed in the receiver, representing a yield of 14% of the acetylene. The temperature was increased to 350° C. After 3 hours, 5.3 ml of liquid was collected, a yield of 51%. Both liquids showed strong peaks at 7–7.3 (ppm downfield from tetramethylsilane reference) in the proton NMR spectra. Analysis of the liquid products from Example II is shown in Table 2.

TABLE 2

| Product (Wt %) | 200° C. | 350° C. |
|---|---|---|
| Benzene | 15.57 | 5.29 |
| Toluene | 10.55 | 3.69 |
| Styrene | 1.85 | 0.86 |
| Total $C_8$ aromatics | 21.95 | 6.99 |
| p-Xylene | 3.02 | 1.01 |
| $C_9$ aromatics | 5.77 | 2.94 |
| Naphthalene | 1.02 | 0.49 |
| 2-Methylnaphthalene | 0.51 | 0.32 |
| 1-Methylnaphthalene | 0.48 | 0.33 |
| $C_{10+}$ Aromatics | 29.01 | 26.21 |
| TOTAL | 86.71 | 47.12 |

EXAMPLE III

To demonstrate the effectiveness of zirconia-alumina catalyst A, moist acetylene at 50 cc/min was passed over 50 ml of adsorption grade alumina as per the method of Example II. At 250° C. over 3 hours, the yield of liquid product was 6%. In the same manner, the yield at 350° C. was 16%. Other catalysts that under identical conditions were either totally inactive or gave only traces of liquids from 200° C. to 400°–450° C. were silica gel, Norite adsorption charcoal, molybdena, molybdenum sulfide, erbium oxide, and zirconia (catalyst F).

EXAMPLES IV-VII

Examples IV-VII were run in the following manner. The catalyst (25 cc) was supported on a quartz wool plug in the center of a 17 inch long quartz tube. The reaction tube was mounted vertically within an electric furnace. All catalysts were calcined overnight in air flowing at 200 ml/min at 500° C. in the reactor. The furnace temperature was then lowered to 350° C. for the reaction. The top of the reactor was fitted with a gas inlet adaptor and a concentric thermal well which projected to the bottom of the catalyst bed. An ice cooled U-tube, optionally containing about 10 cc of isopropanol, was attached to the bottom of the reactor to collect the liquid products. All reactions were run at atmospheric pressure. Acetylene at 45.6 standard ml/min (273 K.°, 1 atmosphere) was bubbled through 3–4 inches of water to obtain a water content of about 3 (mole)% water and then passed through the catalyst. During half hour intervals during the reaction the off-gases were sampled and analyzed by gas chromatography (GC). The total volume of reactor off-gases was measured by a wet-test meter. After 180 minutes on stream, the reaction was ended. The liquid products were collected and weighed. The results of Examples IV-VII are reported in Table 3.

The catalyst was observed to be heavily coked, 1.36 g coke on 39.58 g catalyst in Examples IV and VI.

TABLE 3

| Example | Catalyst | Conversion % of Acetylene | Yield, % of Organic Liquid | Yield % of Coke |
|---|---|---|---|---|
| IV | A $ZrO_2$—$Al_2O_3$, (Alfa) | 59 | 25 | 14 (1.3 g) |
| V | B $ZrO_2$—$Al_2O_3$, (impregnated) | 56 | 19 | nd |
| VI | E $ZrO_2$, precipitated | 26 | 13 | 14 (1.3 g) |
| VII | F $ZrO_2$, (Aldrich) | 9 | 5 | nd | nd — Not determined

EXAMPLE VIII

In the procedure of Example IV, a stream of acetylene, 100 (mole)%, was passed over zirconia-alumina catalyst A. Total gas flow rate was adjusted to give a contact time of 1.9 seconds. Conversion of acetylene was measured by gas chromatography. Initial conversion of acetylene was appproximately 100%. Carbon buildup upon the catalyst was indicated by an increasingly lower conversion rate. After about 60 minutes a rapid decline in conversion of acetylene was observed. After about 90 minutes, conversion of acetylene had dropped to about 40% of acetylene fed. The reaction was then stopped. The catalyst was observed to be heavily coked, 1.2 g coke on 38.6 g catalyst.

EXAMPLE IX

A synthetic product stream from the partial oxidation of methane was passed over zirconia-alumina catalyst A in the manner of Example IV. The composition of the stream was 13.2 (mole)% acetylene, 51.0 (mole)% hydrogen, 25.3 (mole)% carbon monoxide, and 10.5 (mole)% water. The total gas flow rate was adjusted to give a contact time of 1.9 seconds. The average conversion of acetylene over 3 hours was 82%. The yield of organic liquids was 50 (wt)%. The hydrogenation of acetylene to ethylene and ethane accounted for less than 4 (mole)% yield. A wide range of aromatic and aliphatic oxygenated products were formed with a average composition of $C_{13}H_{18}O$. The major components are listed in Table 4.

TABLE 4

Major Components from Acetylene-Water Conversions Over $ZrO_2$—$Al_2O_3$ (Catalyst A)

| Component | Area % |
|---|---|
| Aliphatics [40%] | |
| Acetaldehyde | 1.4 |
| Ethanol | 1.1 |
| Acetone | 1.3 |
| Crotonaldehyde | 3.8 |
| 2-Pentanone | 3.9 |
| 2-Pentene-4-one | 2.6 |
| Methylcyclohexanones | 9.2 |
| Aromatics [60%] | |
| Benzene | 3.0 |
| Toluene | 2.0 |
| o-Xylene | 10.1 |
| o-Methylbenzaldehyde | 6.3 |
| Ethyl Phenols | 8.6 |
| o-Methylacetophenone | 3.2 |
| Higher Alkylphenols | 9.1 |
| Methylethylphenols | 7.5 |

EXAMPLES X-XVI

To evaluate the conversion of acetylene in the presence of steam, 45.6 standard ml/min of acetylene was combined with 22.4 standard ml/min of steam, to obtain a water content of about 33 (mole)% water, and passed over 25 cc of a catalyst in the manner of Example IV. Run time was 180 minutes. The catalyst was observed to be moderately coked, 0.7 g coke on 33.6 of catalyst. A water content of about 33 (mole)% water resulted in an increased yield of organic liquids in Example X, 63%, as compared with the yield of organic liquids in Example IV, 25%, wherein a water content of about 3 (mole)% was present. The results are reported in Table 5. The liquid products from these examples were found to contain the same wide range of aliphatic and aromatic oxygenated products as the product of Example VIII.

TABLE 5

| Example | Catalyst | Conversion % of Acetylene | Yield, % of Organic Liquid | % | Yield of Coke (wt) g |
|---|---|---|---|---|---|
| X | A $ZrO_2$—$Al_2O_3$, (Alfa) | 80 | 63 | 7 | 0.7 |
| XI | B $ZrO_2$—$Al_2O_3$, (impregnated) | 71 | 49 | 2 | 0.16 |
| XII | C 80% $ZrO_2$(E)/$Al_2O_3$ | 59 | 28 | 3 | 0.30 |
| XIII | D 80% $ZrO_2$(F)/$Al_2O_3$ | 17 | 8 | 3 | 0.3 |
| XIV | F $ZrO_2$, (Aldrich) | 5 | 1 | nd | |
| XV | G active alumina | 21 | 6 | 8 | 0.8 |
| XVI | 12.5 cc each of F and G | 17 | 6 | nd | | nd — Not determined

EXAMPLE XVII

To test the effect of higher levels of steam on the conversion of acetylene, a feed stream composed of 5 (mole)% acetylene, 9 (mole)% hydrogen, 16 (mole)% hydrogen and 70 (mole)% water has passed over zirconia-alumina catalyst A in the manner of Example IV. The total gas flow rate was adjusted to give a contact time of 0.65 sec. The average conversion of acetylene was 51%. The liquid product yield was 42 (wt)%. Product distribution was as follows: acetaldehyde, 26%; ethanol, 17%; acetone, 54%; 3-methyl-5-ethylphenol, 4%.

EXAMPLE XVIII

A feed stream consisting of 6.6 (mole)% acetaldehyde, 2.5 (wt)% acetone, 25.3 (mole)% hydrogen and 55.55 (mole)% water was passed over zirconia-alumina catalyst A with a contact time of 1.8 sec at 350° C. for 26 min. Capillary GLC analysis of the product revealed that five major products were formed. 2-Pentanone (39 area %) along with four alkylphenols (61 area %) were found.

EXAMPLE XIX

A feed stream consisting of 16 (mole)% acetylene and 84 (mole)% water was passed over zirconia-alumina catalyst A with a contact time of 0.9 seconds at 350° C. for 3 hours. Capillary analysis of the liquid revealed that 3-methyl-5-ethyl-phenol was the only product formed in more than trace amounts with a carbon number greater than 3.

EXAMPLE XX

A synthetic mixture containing equal amounts of acetaldehyde, acetone, 2-pentanone, cyclohexanone and acetophenone (typical of the products formed in Examples IX-XVI) in tetraethylene glycol as a solvent was prepared. A 20 cc sample of this solution along with 10 g of $CuO$—$Cr_2O_3$—$BaO$ hydrogenation catalyst was loaded in a glass-lined autoclave, charged with 1380 psig of hydrogen, heated to 100° C., and stirred for two hours at 1500 rpm. The autoclave was cooled, vented to atmospheric pressure, and the liquid product was separated from the catalyst. Analysis of the liquid product revealed that all of the carbonyl containing components had been hydrogenated to the corresponding alcohols in at least 85% yield. Approximate research octane numbers for the alcohol products are: ethanol, 130; isopropanol, 117; 2-pentanol; 75; cyclohexanol, 75; 2-phenylethanol, 115.

What is claimed is:

1. A process for the liquefaction of acetylene in a crude acetylene stream comprising acetylene, water, and at least one of methane, carbon dioxide, carbon monoxide, oxygen, nitrogen and hydrogen, wherein the water content of the stream is in the range of from about 0.1 (mole)% to about 70 (mole)% and the mole ratio of acetylene-to-water in the stream is from about 100:1 to about 1:35 in the presence of a zirconia-alumina catalyst wherein the alumina content is in the range from 1 (wt)% to about 10 (wt)%, the zirconia surface area of said catalyst is from about 10 to about 100 $m^2/g$, the surface alumina:zirconium (Al:Zr) atomic ratio is 0.01:1 to 20:1, at a temperature within the range of from about 200° to 500° C. and a pressure of from about 0.5 to 2.0 atmosphere, to form at least one of aromatic hydrocarbons and aromatic and aliphatic oxygenated products.

2. The process of claim 1 wherein said alumina content is in the range of from 1 (wt)% to about 2.5 (wt)% and said surface aluminum:zirconium atomic ratio is in the range of 0.1:1 to 1:1.

3. The process of claim 1 wherein said crude acetylene stream contains methane, carbon dioxide, oxygen, nitrogen, water, hydrogen, carbon monoxide, acetylene and acetylenic compounds.

4. The process of claim 1 wherein the acetylene stream contains up to about 3 mole % water and up to about 97 mole % acetylene, and the product stream comprises benzene, alkylbenzene, and higher aromatics.

5. The process of claim 1 wherein the acetylene stream contains acetylene and water in a 1:4 to 1:30 mole ratio and the product stream comprises acetaldehyde, ethanol, and acetone.

6. The process of claim 1 wherein the acetylene stream contains water and acetylene in about a 1:2 to 2:1 mole ratio and the product stream comprises aromatic and aliphatic oxygenates.

7. The process of claim 1 wherein said temperature is within the range of 300° C. to about 500° C. and pressure is within the range of from about 1.0 to 1.5 atmospheres.

* * * * *